Figure 1:
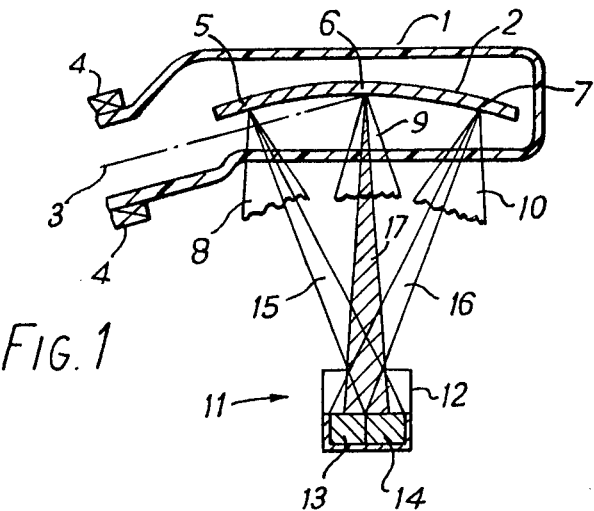

United States Patent [19]

Froggatt

[11] 4,160,909

[45] Jul. 10, 1979

[54] X-RAY TUBE ARRANGEMENTS

[75] Inventor: Robert J. Froggatt, Southall, England

[73] Assignee: E M I Limited, Hayes, England

[21] Appl. No.: 819,578

[22] Filed: Jul. 27, 1977

[30] Foreign Application Priority Data

Aug. 12, 1976 [GB] United Kingdom ............... 76 33555

[51] Int. Cl.² .................................................. H05G 1/30
[52] U.S. Cl. ................................. 250/402; 250/445 T; 250/385
[58] Field of Search ........... 250/401, 402, 397, 445 T, 250/490, 491, 385

[56] References Cited

U.S. PATENT DOCUMENTS

| 3,838,284 | 9/1974 | McIntyre et al. | 250/397 |
| 3,852,605 | 12/1974 | Watanabe et al. | 250/402 |
| 3,955,089 | 5/1976 | McIntyre et al. | 250/491 |
| 3,975,640 | 8/1976 | Boux et al. | 250/385 |

Primary Examiner—Bruce C. Anderson
Attorney, Agent, or Firm—Cooper, Dunham, Clark, Griffin & Moran

[57] ABSTRACT

In order to monitor the progress of a deflected electron beam across the target of an X-ray tube, the emitted X-radiation is monitored, by allowing radiation to impinge, via a common aperture, upon two or more radiation sensitive detectors, to produce a progress signal which is compared with an ideal progress signal to generate error signals in the event of departure of the monitored progress from the ideal progress.

5 Claims, 7 Drawing Figures

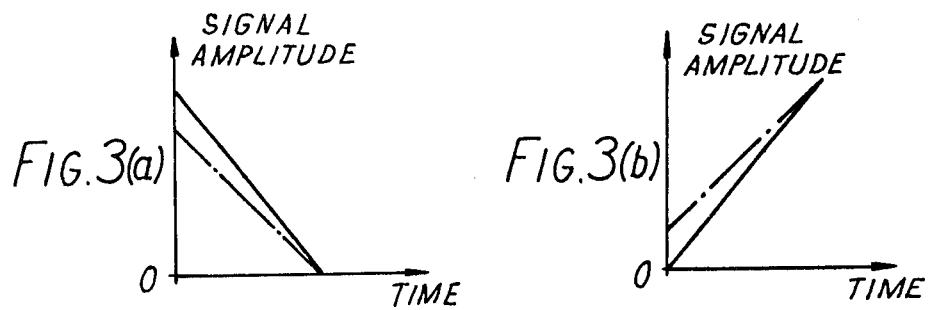
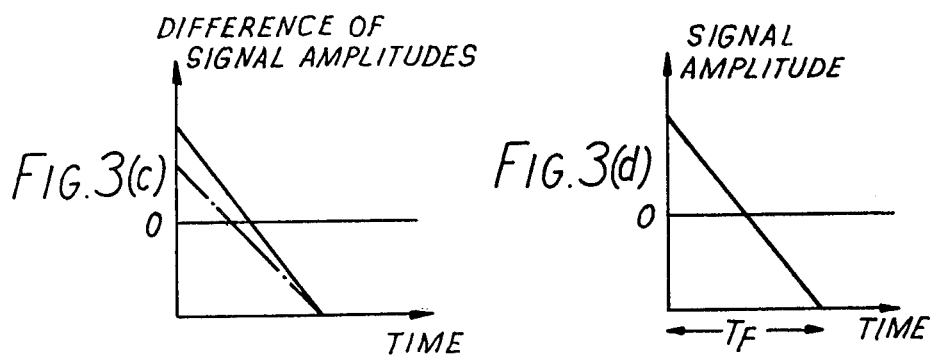
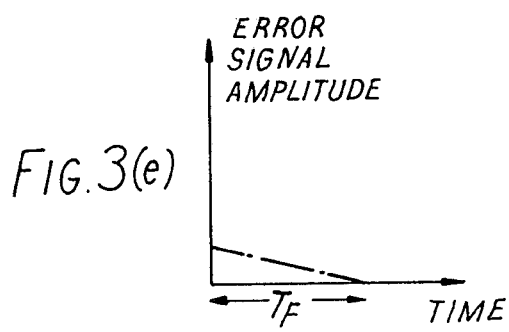

X-RAY TUBE ARRANGEMENTS

The present invention relates to X-ray tube arrangements, and it relates more particularly to such arrangements for use in radiographic apparatus for performing computerised axial tomography. Such apparatus is described and claimed in U.S. Pat. No. 3,778,614 and developments of such apparatus are described, for example, in the specification of U.S. application Ser. No. 630,779 filed Nov. 11, 1975 (now U.S. Pat. No. 4,010,370) and in the specification of U.S. application Ser. No. 733,941 filed Oct. 19, 1976 (now U.S. Pat. No. 4,115,698) wherein X-ray tubes incorporating an elongated X-ray emissive target/anode member are described, the tube in each case having facilities for scanning the electron beam thereof over said member so as to cause the radiation generated by the tube to shift its point of origin.

The present invention relates to arrangements including X-ray tubes of the kind referred to above (hereinafter termed X-ray tubes with deflection) and is connected with a problem which arises in accurately monitoring the deflection of the said electron beam across said X-ray emissive member. The said deflection must be accurately monitored because it determines the point of origin of the X-ray emission at any time and thus determines the origin of beam paths along which radiation is projected. The disposition of these beam paths has to be accurately known in relation to a cross-sectional slice through a patient's body, through which slice the radiation is projected, in order that signals indicative of the absorption suffered by the radiation in traversing said beam paths can be processed to produce an accurate evaluation of the variation of absorption of said radiation over said slice.

U.S. application Ser. No. 799,712 filed May 23, 1977 in the name of Colin G. Oliver and assigned to the same assignee as this application, discloses some techniques for effecting the above-mentioned monitoring, and the present invention relates to another technique for effecting said monitoring.

According to the invention there is provided an arrangement for monitoring repetitive movement of a a source of radiation along an elongated, X-ray emissive anode/target member, included in an X-ray tube, as a result of repetitive deflection of a beam of electrons, generated in said tube, to and fro along said member, wherein the deflection is effected by deflection means associated with the tube and supplied with repetitively occuring deflection waveforms, the arrangement including detector means having a plurality of detector devices disposed to receive said radiation through a common aperture dimensioned to cause the radiation to shift across said devices as said movement occurs, said devices producing electrical output signals indicative of the actual progress of said movement, means for generating datum electrical signals indicative of the desired progress of said movement, means for comparing said electrical output signals with said datum electrical signals to produce error signals indicative of discrepancy between said actual progress and said desired progress, and means utilising said error signals to modify said deflection waveforms in a sense tending to reduce such discrepancy.

Figure 2:
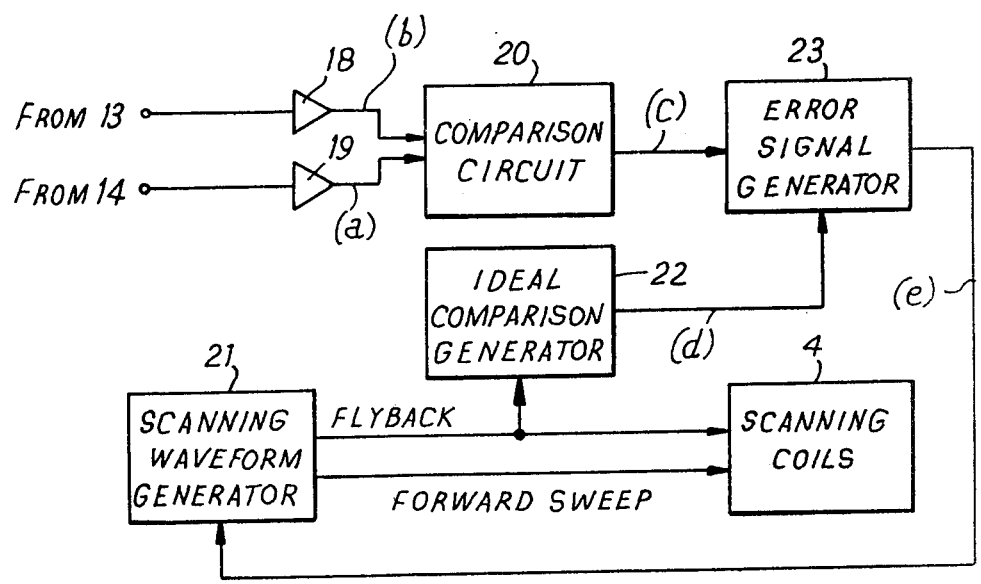

In order that the invention may be clearly understood and readily carried into effect, one embodiment thereof will now be described, by way of example only, with reference to the accompanying drawings of which:

FIG. 1 shows, in schematic and cross-sectional form, some of the components of an arrangement in accordance with one example of the invention, FIG. 2 shows, in block diagrammatic form, a circuit forming part of said example of the invention, and FIGS. 3(a) to 3(e) show, respectively, graphs indicative of the operation of the circuit shown in FIG. 2.

Referring now to FIG. 1, an X-ray tube 1 is mounted on an apertured turntable (not shown) for rotation about a patient's body (not shown) disposed in said aperture. Suitable arrangements of turntables and associated components are described in the aforementioned patents and thus will not be further described herein. The tube 1 contains an elongated, X-ray emissive target-/anode member 2 over which an electron beam 3 can be deflected by means of deflection coils 4 (see also FIG. 2). The arrangement is such that a fan-shaped spread of X-rays is emitted from the member 2 from whichever region thereof the beam 3 is incident upon a given time. The spreads of radiation emitted from three points 5, 6 and 7 on said member 2 are shown at 8,9 and 10 respectively. These particular points have been chosen because points 5 and 7 represent the required limits of deflection whereas point 6 represents the center of the deflectional movement of beam 3 along member 2. The spreads such as 8, 9 and 10 are caused by suitable collimating means (not shown) to irradiate a cross-sectional slice of the patient.

In accordance with this example of the invention, some of the radiation produced by the tube 1 which would have been outside the bounds of said slice and which would have been removed, in any event, by said collimation, is allowed to impinge upon a monitoring detection unit 11. The unit 11 includes an apertured housing 12 and a pair of radiation-sensitive detectors 13, 14 which may comprise, for example, sodium iodide or cesium iodide crystals with associated photomultiplier channels or photodiodes. Such detectors are well known in the art. The unit 11 is so dimensioned and located in relation to the tube 1 that the relative proportions of radiation impinging on the two detectors 13, 14 changes as the electron beam 3 is deflected across the member 2. It can be seen from FIG. 1 that when the electron beam 3 is incident upon point 5 of the member 2, radiation incident through the aperture in the housing 12 follows a path 15 and is incident substantially only on the detector 14. On the other hand, when the electron beam 3 is incident upon point 7 of member 2, then the radiation entering unit 11 follows a path 16 and impinges substantially only on detector 13. In the central part of the scan, radiation following a path 17 to the unit 11 impinges to a substantially equal extent upon both detectors 13 and 14. Clearly positions between 5 and 6 and between 6 and 7 give rise to intermediate amounts of radiation impinging upon the two detectors.

Referring now to FIG. 2, electrical output signals from the detectors 13 and 14 are applied respectively to amplifiers 18 and 19 and are thence applied to a comparison circuit 20 which can conveniently be constituted by a differencing amplifier of known kind.

The deflection waveforms for the deflection coils 4 are derived from a scanning waveform generator 21, which preferably generates substantially sawtooth waveforms for forward sweep and flyback respectively; the timing being such that, typically, flyback is effected in ten percent of the forward sweep period. The flyback sawtooth waveform is also applied, as an initiating control signal, to an ideal comparison generator circuit 22 which generates a waveform which represents what the output of circuit 20 should be if the deflection were of the correct amplitude and positioning. The output signals from circuits 20 and 22 are compared (for example differenced) in an error signal generating circuit 23, which generates error signals indicative of the sense and magnitude of discrepancies between the signals applied thereto and such error signals are applied to the scanning waveform generator circuits 21 in a sense tending to reduce such discrepancies.

Referring now to FIG. 3, there are shown five idealised graphs, 3(a) to 3(e), representing waveforms which may occur at the points of the circuit at FIG. 2 bearing the same reference letters. Considering first the graphs drawn in solid lines only, these show the situation which occurs if the deflection amplitude and positioning is exactly correct. Thus FIG. 3(a) shows that the output of detector 14 starts at the maximum value (due to radiation impinging thereon via path 15) and decreases lineraly to zero by the time that radiation is entering the unit 11 (FIG. 1) via path 16. It will be appreciated that the actual output from the detector 14 itself may not be linear, but it can be linearised by suitable selection of the characteristics of the amplifier 19. Similar remarks apply, of course, to detector 13 and amplifier 18.

FIG. 3(b) shows the linearised output of detector 13 over the same period as that considered in relation to FIG. 3(a). The said output increases linearly from zero to a maximum value in inverse sense to the graph of FIG. 3(a).

FIG. 3(c) shows (on a different vertical scale to FIGS. 3(a) and 3(b)) the difference between the signals shown in these Figures as generated by circuit 20. FIG. 3(d) shows the ideal difference waveform as generated by the generator 22. In this particular case, the output of the error signal generator would be zero, as there is no discrepancy between the outputs of circuits 20 and 22.

If now the dashed lines on the graphs 3(a) to 3(c) and 3(e) are considered, this represents an error condition in which the forward scan commences to the right of point 5 (FIG. 1) but terminates at point 7 (FIG. 1). Thus the starting scan position is in error, as is the scan amplitude. The detector 14 thus does not receive as much radiation as it should at the start of the deflection, whereas the detector 13 is receiving more radiation than it should at that time. The amounts of radiation detected by the two detectors are, however, correct at the end of the forward deflection period $T_F$. The error shows up in FIG. 3(c) as a change in slope of the graph, and taking the difference of the graphs shown in 3(d)—solid line—and 3(c)—broken line—give rise to the error signal indicated by the broken line in FIG. 3(e). It will be noted that this error signal is indicative at any instant of the discrepancy between the outputs of circuits 20 and 22 and it is thus applied on line, i.e. without integration, to the deflection waveform generating circuits 21. The error signal once incorporated into the deflection waveform becomes an integral part of it, so that the next forward sweep of the beam 3 over the member 2 is effected with a waveform which is predistorted in accordance with the error signal applied to circuit 21 during the preceding forward deflection interval. By this means, the error signal produced by circuit 23 tends to reduce to zero.

Although this invention has been described in relation to a particular example thereof, it is not limited to said example. For example, the unit 11 could be replaced by a number of detectors each viewing a respective small portion of the member 2 through a common, narrow aperture so that the progress of the deflection causes sequential output signals to be produced by the detectors.

As an addition to either of the monitoring arrangements described hereinbefore, scan reversal monitoring as described in U.S. patent application Ser. No. 814,334, filed July 11, 1977 (now U.S. Pat. No. 4,112,397) can be employed.

What I claim is:

1. An arrangement for monitoring repetitive movement of a source of X-radiation along an elongated, X-ray emissive anode/target member, included in an X-ray tube, as a result of repetitive deflection of a beam of electrons, generated in said tubes, to and fro along said member, wherein the deflection is effected by deflection means associated with the tube and supplied with repetitively occurring deflection waveforms, the arrangement including detector means having a plurality of detector devices disposed to receive said radiation through a common aperture dimensioned to cause the radiation to shift across said devices as said movement occurs, said devices producing electrical output signals indicative of the actual progress of said movement, means for generating datum electrical signals indicative of the desired progress of said movement, means for comparing said electrical output signals with said datum electrical signals to produce error signals indicative of discrepancy between said actual progress and said desired progress, and means utilizing said error signals to modify said deflection waveforms in a sense tending to reduce such discrepancy.

2. An arrangement according to claim 1 wherein said deflection means includes deflection coil means and a scanning waveform generator operatively connected to said coil means, said deflection means causing said beam of electrons to alternately sweep substantially linearly along said member in one direction at a relatively slow rate and fly back in the other direction at a relatively rapid rate.

3. An arrangement according to claim 2 wherein said detector means includes two detector devices, one of which receives a majority of the radiation passing through said aperture at the commencement of a sweep.

4. Apparatus according to claim 3 wherein each of said detector devices comprises a scintillator crystal operatively coupled to a converter for converting optical radiation into electrical signals.

5. Apparatus according to claim 4 wherein each of said converters comprises a photomultiplier tube.

* * * * *